United States Patent
Nakamura et al.

(10) Patent No.: US 9,335,261 B2
(45) Date of Patent: May 10, 2016

(54) TIME-DOMAIN SPECTROSCOPY AND TIME-DOMAIN SPECTROSCOPIC ANALYSIS SYSTEM

(75) Inventors: Takahiro Nakamura, Tokyo (JP); Nobuhiro Shiramizu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 72 days.

(21) Appl. No.: 14/382,802

(22) PCT Filed: Mar. 30, 2012

(86) PCT No.: PCT/JP2012/002221
§ 371 (c)(1),
(2), (4) Date: Sep. 4, 2014

(87) PCT Pub. No.: WO2013/145020
PCT Pub. Date: Oct. 3, 2013

(65) Prior Publication Data
US 2015/0028211 A1    Jan. 29, 2015

(51) Int. Cl.
*G01N 21/3586* (2014.01)

(52) U.S. Cl.
CPC .. *G01N 21/3586* (2013.01); *G01N 2201/06113* (2013.01)

(58) Field of Classification Search
CPC ................. G01N 21/3586; G01N 2201/06113
See application file for complete search history.

(56) References Cited

U.S. PATENT DOCUMENTS

| | | | | |
|---|---|---|---|---|
| 2003/0214360 A1* | 11/2003 | Motoyoshi | ................ | H03L 7/18 331/16 |
| 2004/0149914 A1* | 8/2004 | Abrahamsson | ...... | G01N 21/359 250/343 |
| 2008/0165355 A1 | 7/2008 | Yasui et al. | | |
| 2008/0239317 A1* | 10/2008 | Schulkin | ................... | G01J 4/00 356/365 |
| 2009/0162076 A1* | 6/2009 | Wang | ..................... | G01N 17/02 398/185 |
| 2010/0002737 A1 | 1/2010 | Rausch et al. | | |

FOREIGN PATENT DOCUMENTS

| | | |
|---|---|---|
| JP | 2009-150811 A | 7/2009 |
| JP | 2011-242180 A | 12/2011 |
| WO | 2006/092874 A1 | 9/2006 |

OTHER PUBLICATIONS

Tani et al., "Ultrafast Terahertz Wave Measurement Based on a New Asynchronous Sampling Method", IEICE Technical Report, May 21, 2010, pp. 7-8.

Tani et al "Research and Development for Ultrafast Terahertz Time-Domain Spectroscopy System", Ensekigai Ryoiki Kaihatsu Kenkyu, Jul. 2010, pp. 99-106.

\* cited by examiner

*Primary Examiner* — David Porta
*Assistant Examiner* — Mindy Vu
(74) *Attorney, Agent, or Firm* — Mattingly & Malur, PC

(57) ABSTRACT

The time-domain spectroscopy analysis system includes a splitter for splitting pulsed light entered, a variable delayer for delaying timing of a first part of the pulsed light split by the splitter, an electromagnetic wave generator for converting a second part of the pulsed light split by the splitter into an electromagnetic wave, a detector for detecting measurement data from a pulse having passed through a measurement object subjected to the electromagnetic wave emitted from the electromagnetic wave generator, and the pulse outputted from the variable delayer, and a comparator for detecting a phase difference between the pulsed light before being entered into the electromagnetic wave generator and the pulsed light outputted from the variable delayer, wherein a result obtained by the comparator is fed back to the variable delayer.

12 Claims, 9 Drawing Sheets

TIME-DOMAIN SPECTROSCOPY AND TIME-DOMAIN SPECTROSCOPIC ANALYSIS SYSTEM

TECHNICAL FIELD

The present invention relates to time-domain spectroscopies and time-domain spectroscopic analysis systems, and more particularly, to effective techniques when applied to spectroscopies for a terahertz range (0.1 to 100 THz).

BACKGROUND ART

For example, PTL 1 and PTL 2 disclose time-domain spectroscopies in an asynchronous sampling system using two femtosecond pulse lasers.

CITATION LIST

Patent Literatures

PTL 1: JP 2011-242180 A
PTL 2: US 2010/0002737 A

SUMMARY OF INVENTION

Technical Problem

For example, a time-domain spectroscopy includes a femtosecond pulse laser for outputting a train of light pulses with a pulse width of 1 ps or less, a pulse generator such as a photoconductive switch for emitting a pulsed terahertz wave in a wide range up to terahertz with light pulses of the pulse laser as pump light, and a pulse detector for detecting the intensity of a pulsed terahertz wave at the timing of input of a light pulse as prove light. In the time-domain spectroscopy, it is necessary to vary the timing of input of probe light into the detector with respect to pump light to measure a pulsed terahertz wave emitted by the pulse generator at a plurality of points in the time domain. Therefore, as in FIG. 1 in PTL 1, it has conventionally been required to provide a variable delayer in an optical path of probe light to measure while varying delay time provided by the delayer. For the delayer, a structure for mechanically changing the position of a reflector is used, thus posing a problem of increased control time of the delay time, and increased time for measurement of from some seconds to some minutes. To this problem, there has been developed a time-domain spectroscopy in an asynchronous sampling system in which two femtosecond pulse lasers are used to provide lasers to supply pump light and probe light, separately, and the pulse periods of the two lasers are slightly changed to omit a variable delayer for speed enhancement (PTL 1). The use of this system eliminates the need for a mechanical control mechanism and thus is suitable for speed enhancement. However, it requires as much as two expensive femtosecond pulse lasers, posing a problem of an expensive price of the time-domain spectroscopy. Further, it poses a problem that jitter in a laser pulse deteriorates the signal-to-noise ratio (SN ratio). Jitter is a distribution of timing of a laser pulse. Thus an increase in jitter fluctuates a time difference between pump light and probe light. Therefore, it poses a problem that a deviation from a required time difference occurs, producing noise of frequencies in a Fourier transform, and deteriorating the SN ratio.

To the above-described problem of the spectroscopy becoming expensive, there has been developed a difference frequency synchronous sampling system in which a single femtosecond pulse laser is used to eliminate delay variation by variable delayer control (PTL 2). In this system, both pump light and probe light are supplied from the same laser, but probe light is supplied with a delay of light pulse N periods (N is a positive integer). The pulse period of the laser is controlled to vary continuously. By delaying probe light by one period with respect to pump light, timing difference between probe light and pump light varies continuously. As a result, terahertz electromagnetic wave pulses can be detected with different timings to obtain them at a plurality of points, thereby to obtain a waveform of the terahertz electromagnetic wave pulses.

As described above, the difference frequency synchronous sampling system can eliminate the need for a mechanical control mechanism and is suitable for speed enhancement. However, there remains a problem of deterioration in the SN ratio due to jitter, as in the asynchronous sampling system. The pulse period of the laser needs to be varied, resulting in an increase in jitter compared with the case where the pulse period is fixed.

In addition to the problem of SN ratio deterioration due to jitter as above, the difference frequency synchronous sampling system has some problems. FIG. 7 is a block diagram illustrating an example of a schematic configuration of a time-domain spectroscopy considered as a premise of the present invention. A time-domain spectroscopy (TDS) shown in FIG. 7 includes a femtosecond pulse laser (fsL) 19, a light pulse period controller (PCON) 23, a pulse generator (GEN) 15, a pulse detector (DET) 14, and a delayer (DEL) 101. The period of light pulses outputted by the fsL 19 is controlled by a control signal such as a voltage or a clock fed from the PCON 23. An outputted light pulse is split into two parts by a half mirror or the like. One part of the split light pulse is entered into the GEN 15 as pump light. The GEN 15 emits a pulsed terahertz wave. The other part of the light pulse is entered into the DET 14 as probe light after a delay time of one period of the light pulse period by the delayer. A current $I_{DET}$ corresponding to the signal intensity of a pulsed terahertz wave propagated to the DET 14 at the timing of input of probe light is outputted from the DET 14. A first problem in the configuration example in FIG. 7 is fluctuations in delay time produced by the DEL 101 for probe light. FIG. 8 shows waveforms of pump light pulses and probe light pulses during correct functioning. During correct functioning, the timing of probe light pulses is controlled so as to sweep before and after that of pump light. The conventional delayer 101 is formed by a fiber cable of a required optical path length, for example. However, delay time provided by a fiber cable is affected by temperature and atmospheric pressure around the fiber cable, and thus fluctuates due to a change in temperature and atmospheric pressure. Therefore, as shown in FIG. 9, the timing of probe light deviates, and a range in which a signal is greatest cannot be obtained. This can lower an output signal of the detector, and deteriorate the SN ratio. The deterioration in SN ratio causes the necessity of increasing the number of measurements to be added up and averaged in order to compensate for the deterioration, and can increase time for analysis.

A second problem is a problem due to the non-linearity of the pulsed laser with respect to a control signal. FIG. 10 shows an example of the characteristics of the pulsed laser controlling an inverted number of a pulse period (that is a pulse repetition frequency) with respect to a control signal. Pulse period control of the pulsed laser includes a method of controlling by voltage, a method of feeding a clock for synchronization with the clock, and the like. Here the method of controlling by voltage will be considered. Ideally, it is controlled linearly as shown by a dotted line, but in practice, it exhibits non-linear characteristics as shown by a solid line. In order to control the timing difference between pump light and probe light precisely using the pulsed laser with the control characteristics exhibiting non-linear characteristics, for example, there is a method of controlling the pulse period of the pulsed laser by feedback using a phase locked loop (PLL) circuit. However, a PLL circuit requires a generator of a reference frequency to be referenced, and a spurious tone due to the reference frequency is superimposed on a pulse laser output. A spurious tone is a part of jitter, and thus can deteriorate the SN ratio. Deterioration in the SN ratio causes the necessity of increasing the number of measurements to be added up and averaged in order to compensate for the deterioration, and can increase time for analysis.

Solution to Problem

The outline of a typical embodiment of the present invention disclosed in the present application will be briefly described as follows.

A time-domain spectroscopy includes: a splitter for splitting pulsed light entered; a variable delayer for delaying timing of a first part of the pulsed light split by the splitter; an electromagnetic wave generator for converting a second part of the pulsed light split by the splitter into an electromagnetic wave; a detector for detecting measurement data from a pulse having passed through a measurement object subjected to the electromagnetic wave emitted from the electromagnetic wave generator, and the pulse outputted from the variable delayer; and a comparator for detecting a phase difference between the pulsed light before being entered into the electromagnetic wave generator and the pulsed light outputted from the variable delayer, wherein a result obtained by the comparator is fed back to the variable delayer.

Alternatively, a time-domain spectroscopy includes: a splitter for splitting pulsed light entered; a variable delayer for delaying timing of a first part of the pulsed light split by the splitter; an electromagnetic wave generator for converting a second part of the pulsed light split by the splitter into an electromagnetic wave; a detector for detecting measurement data from a pulse having passed through a measurement object subjected to the electromagnetic wave emitted from the electromagnetic wave generator, and the pulse outputted from the variable delayer; and a comparator for detecting a phase difference between the pulsed light before being entered into the electromagnetic wave generator and the pulsed light outputted from the variable delayer, wherein data obtained by the comparator and the measurement data are used to obtain a measurement result of the measurement object.

Advantageous Effects of Invention

According to the invention, a time-domain spectroscopy and a time-domain spectroscopic analysis system can improve the SN ratio of a frequency spectrum analyzed.

DESCRIPTION OF EMBODIMENTS

Figure 1:
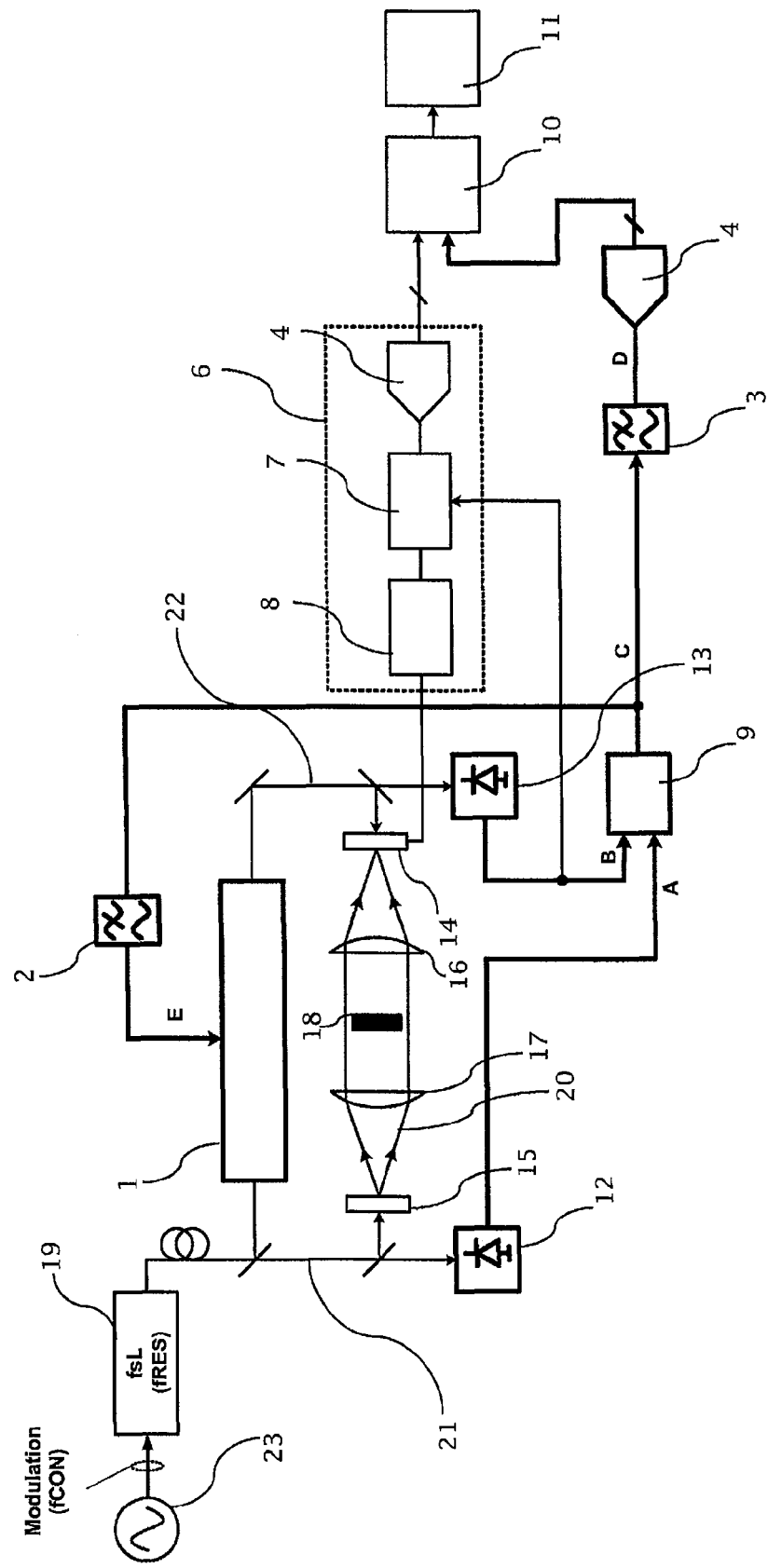
FIG. 1 is a block diagram illustrating an example of a schematic configuration of a time-domain spectroscopy according to Embodiment 1 of the present invention.

Although the following description of embodiments are divided into a plurality of sections or embodiments when it is necessary for convenience, they are not independent of each another except when specified otherwise, and are in such relationships that one is a modification, details, or a supplementary explanation of apart or all of the other. When the number of an element (including a number of articles, a numerical value, an amount, and a range) or the like is referred to in the following embodiments, it is not limited to a specified number except when specified otherwise and when it is theoretically and obviously limited to the specified number, and it maybe more than or less than or equal to the specified number.

Further, in the following embodiments, it is needless to say that the components (including element steps and the like) are not necessarily essential except when specified otherwise and when they are considered theoretically and obviously essential. Likewise, in the following embodiments, when the shapes, the positional relationships, and the like of the components are referred to, they are intended to include those substantially close to or similar to the shapes and others, and the like except when specified otherwise and when it is theoretically and obviously not the case. The same applies to the above-described numerical value and range.

For a femtosecond pulse laser in the embodiments, a solid-state laser such as a fiber laser or a titanium-sapphire laser, a neodymium-glass laser, or a semiconductor laser is preferably used, which are not particularly limiting. The femtosecond pulse laser preferably has a pulse width of 100 femtoseconds or less, but it is not intended to exclude pulsed lasers exceeding 100 femtoseconds.

Hereinafter, embodiments of the present invention will be described in detail with reference to the drawings. In all the drawings for illustrating the embodiments, like members are denoted by like reference numerals in principle, and redundant descriptions thereof will not be made.

Embodiment 1

Schematic Configuration of Time-Domain Spectroscopy

FIG. 1 is a block diagram illustrating an example of a schematic configuration of a time-domain spectroscopy in a difference frequency synchronous sampling system according to Embodiment 1 of the present invention. The time-domain spectroscopy shown in FIG. 1 includes a femtosecond pulse laser (fsL) 19, a light pulse period controller (PCON) 23, a pulse generator (GEN) 15, a pulse detector (DET) 14, a variable delayer (VDEL) 1, photodetectors (PDETs) 12 and 13, a phase comparator (phase frequency detector: PFD) 9, low-pass filters (LPFs) 2 and 3, analog-to-digital converters (ADCs) 4 and 5, a detector output processing unit (OPU) 6, a computer (personal computer: PC) 10, and a display (DIS) 11 for displaying results of analysis conducted in the PC 10.

The laser 19 outputs pulsed light at intervals of a period T (repetition frequency $f_{RES}=1/T$). The laser 19 includes a period variable terminal for being able to vary the period. $f_{RES}$ is about 100 MHz, but is not particularly limited thereto.

An output of the PCON 23 is fed into the period variable terminal of the laser 19 to control the period T of light pulses outputted by the laser 19. An output of the PCON 23 differs in form, depending on a period control mechanism of the laser 19, and may be a voltage or a clock signal. In this example, it is a voltage signal, and is a periodic signal such as a sine wave, a triangular wave, or a sawtooth wave (period $T_{CON}$, frequency $f_{CON}$). A light pulse outputted from the laser 19 is split by a splitter such as a mirror into light to enter the VDEL 1 and light to enter the GEN 15.

For the GEN 15 and the DET 14, a low-temperature growth GaAs photoconductive switch, an InGaAs photoconductive switch, or a DAST crystal is generally used, which is not particularly limiting. A light pulse (pump light) entered into the GEN 15 generates free electrons in the GEN 15. The free electrons are accelerated by a voltage applied, generating a terahertz electromagnetic wave pulse. That is, an electromagnetic wave pulse corresponding to a light pulse entered is generated. The electromagnetic wave pulse is applied to a measurement object 18.

The VDEL 1 is a variable delayer including a piezoelectric element, and provided with a delay time control terminal for controlling delay time, but is not particularly limited thereto. A voltage signal or a current signal fed into the delay control terminal controls a light pulse transit time spent until a light pulse signal entered into the VDEL 1 is outputted from the VDEL 1. Delay time provided by the VDEL 1 is controlled to be near N times (N is a positive integer) the light pulse period T.

A light pulse (probe light) entered into the DET 14 generates free electrons in the DET 14, outputting a current signal in proportion to a terahertz electric field at the position of the DET 14 at the instant (a terahertz electromagnetic wave generated in the GEN 15, passing through the measurement object 18, and entering the DET 14). The current signal outputted from the DET 14 is converted into a voltage signal and amplified in the OPU 6 to be a piece of data, and fed into the computer PC 10 that performs a Fourier transform.

At the implementation of a Fourier transform, when the timing difference between the pump light and the probe light is definite, the timing difference is used to implement a Fourier transform for conversion into frequency range data. When the delay time provided by the VDEL 1 fluctuates or when jitter is superimposed as described in Solution to Problem, a deviation from a required timing difference occurs, deteriorating the SN ratio.

To this problem, a feedback structure including the PDETs 12 and 13, the PFD 9, and the LPF 2 can solve the problem. The PDETs 12 and 13 convert light pulses of pump light and probe light into electrical signals, respectively. The electrical signals resulting from conversion are compared in the PFD 9 to detect a timing difference between them. The detected timing difference is outputted as an electrical signal. The LPF 2 passes only a low-frequency signal, which is fed into the VDEL 1. A cutoff frequency of the LPF 2 is required to be sufficiently small compared with the frequency $f_{CON}$ of a control signal outputted by the PCON 23, and is preferably one tenth or less thereof. Since the feedback structure including the PDETs 12 and 13, the PFD 9, and the LPF 2 is a feedback structure for making the mean value of the timing difference between pump light and probe light zero, when the cutoff frequency of the LPF 2 is more than or equal to $f_{CON}$, the VDEL 1 is controlled to make the timing difference zero at all times. When the cutoff frequency of the LPF 2 is sufficiently small compared with $f_{CON}$, the VDEL 1 functions to cancel only a fluctuation slower than $f_{CON}$. Fluctuations such as in temperature and atmospheric pressure are slow, and thus can be compensated for sufficiently by this feedback structure. A low-frequency component of jitter can also be compensated for by this feedback structure. By using the invented feedback structure, the SN ratio of data after a Fourier transform can be improved, and thus the number of times of adding up data can be reduced for speed enhancement.

Deterioration in the SN ratio due to a jitter component more than or equal to the cutoff frequency of the LPF 2 and the non-linear characteristics of the laser 19 can be solved by a mechanism of extracting timing difference information, using the LPF 3 and the ADC 4. An electrical signal outputted from the PFD 9 is also fed into the LPF 3. A cutoff frequency of the LPF 3 is required to be more than or equal to $f_{CON}$, and is preferably three times more than or equal to $f_{CON}$. An output of the LPF 3 is converted by the ADC 4 into a digital signal, which is fed into the computer. An output of the LPF 3 includes transition information of the timing difference between pump light and probe light. By setting the cutoff frequency of the LPF 3 three times more than or equal to $f_{CON}$, the output includes components up to second-order distortion and third-order distortion of the non-linear characteristics of the laser 19. The output also includes jitter components more than or equal to the cutoff frequency of the LPF 3, which cannot be compensated for by the above-described feedback structure. Therefore, the output of the LPF 3 is transmitted to the computer as information on the actual timing difference between the pump light and the probe light. By implementing a Fourier transform using the timing difference, deterioration in the SN ratio due to the non-linear characteristics of the laser 19 and jitter components more than or equal to the cutoff frequency of the LPF 2 can be improved. By using the invented mechanism for extracting timing difference information, deterioration in the SN ratio due to the non-linear characteristics of the laser 19 and jitter components more than or equal to the cutoff frequency of the LPF 2 can be improved, and thus the SN ratio of data after a Fourier transform can be further improved compared with the case where only the above-described feedback structure is used, and the number of times of adding up data can be reduced for speed enhancement.

Only by either one of the above-described feedback structure and the mechanism for extracting timing difference information, an SN-ratio improvement effect can be expected. When only the latter is used, it is necessary to increase cumulative time for extracting fluctuations in temperature and atmospheric pressure and low-frequency jitter components. A single sweep of timing difference is completed at the inverse $1/f_{CON}$ of the frequency of a pulse period control signal of the fsL. Addition for a time longer than $1/f_{CON}$ is required, and thus it is required to increase the measurement time. When both of them are used, in addition to the SN ratio improvement effect, a measurement time reduction becomes possible.

Based on the above, the invention described in this example is a time-domain spectroscopy that includes the splitter for splitting pulsed light entered, the variable delayer 1 for delaying timing of a first part of the pulsed light split by the splitter, the electromagnetic wave generator 15 for converting a second part of the pulsed light split by the splitter into an electromagnetic wave, the detector 14 for detecting measurement data from a pulse having passed through the measurement object 18 subjected to the electromagnetic wave emitted from the electromagnetic wave generator 15, and the pulse outputted from the variable delayer 1, and the comparator 9 for detecting a phase difference between the pulsed light before being entered into the electromagnetic wave generator 15 and the pulsed light outputted from the variable delayer 1, wherein a result obtained by the comparator 9 is fed back to the variable delayer 1.

Alternatively, a time-domain spectroscopy includes the splitter for splitting pulsed light entered, the variable delayer 1 for delaying timing of a first part of the pulsed light split by the splitter, the electromagnetic wave generator 15 for converting a second part of the pulsed light split by the splitter into an electromagnetic wave, the detector 14 for detecting measurement data from a pulse having passed through the measurement object 18 subjected to the electromagnetic wave emitted from the electromagnetic wave generator 15, and the pulse outputted from the variable delayer 1, and the comparator 9 for detecting a phase difference between the pulsed light before being entered into the electromagnetic wave generator 14 and the pulsed light outputted from the variable delayer 1, wherein data obtained by the comparator 9 and the measurement data are used to obtain a measurement result of the measurement object 18.

Figure 2:
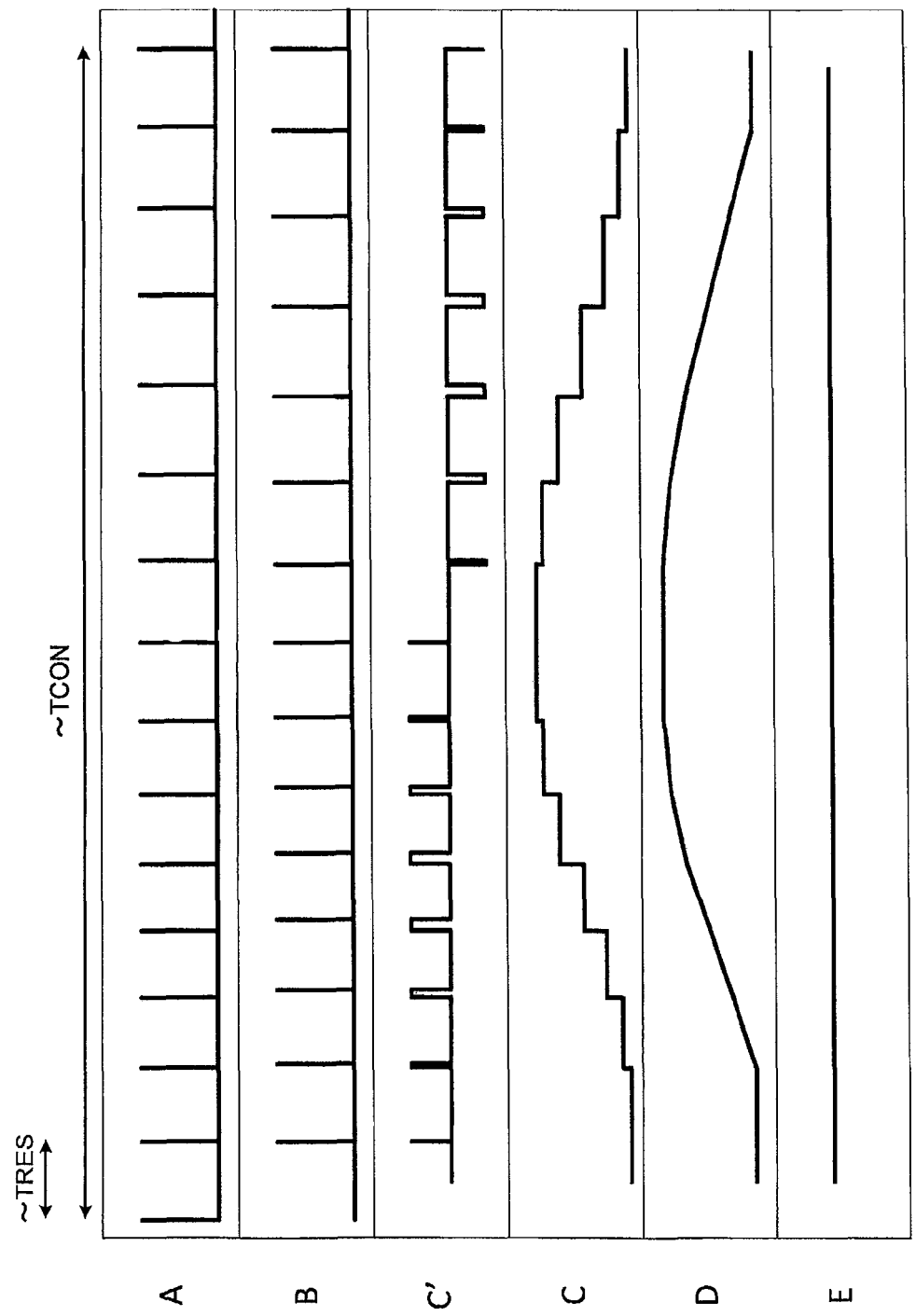
FIG. 2 is an explanatory diagram illustrating the respective signal waveforms of nodes in the time-domain spectroscopy in FIG. 1.

Voltage or current waveforms at nodes (A, B, C, D, and E) in the configuration in FIG. 1 are shown in FIG. 2. In FIG. 2, the PCON 23 outputs a sine wave, by which the pulse period of the laser 19 is controlled. At nodes A and B, light pulses of pump light and probe light are converted into voltage signals, respectively. The PFD 9 outputs a signal proportional to a timing difference between the voltage signals. Here, an example of forming the PFD 9 with a charge pump circuit and a capacity C1, which is a typical structure, is illustrated. The waveform of C' is a waveform of a current signal outputted from the charge pump circuit, which has pulse widths proportional to timing differences between voltage waveforms of the PDETs 12 and 13. A current pulse outputted from the charge pump circuit charges or discharges the C1, and the voltage output of the PFD 9 becomes the waveform of C. The output of the PFD 9 is fed into the LPFs 3 and 2 to be the waveforms of D and E, respectively. At D, the waveform is close to the PCON 23 output since frequency components more than or equal to $f_{CON}$ pass through the LPF 3, and also is a signal including jitter and the non-linear characteristics of the laser 19. At E, the waveform has little fluctuation when viewed for only one period of the PCON 23 output since only frequencies sufficiently smaller than $f_{CON}$ is allowed to pass, but fluctuates with respect to fluctuations in temperature and atmospheric pressure.

<<Configuration Example of Detector Output Processing Unit>>

FIG. 1 also shows an example of a detailed configuration of the detector output processing unit OPU 6 in the time-domain spectroscopy system. Although a conventional detector output processing system using a lock-in amplifier can be used for processing into required data, use of the present configuration can provide further speed enhancement. In the example of FIG. 1, an output current signal of the DET 14 is turned into a voltage signal and amplified by a current-to-voltage conversion amplifier (IV-AMP) 8. The amplified voltage signal is turned into a detector output at each probe light pulse incident timing by a sample-and-hold circuit (SHC) 7 since an output signal of the PDET 13 or 12 fed separately is used as a clock, and is converted by the ADC 5 into a digital signal to be transmitted to the computer PC 10. This configuration allows for monitoring of a detector output at all probe light pulse incident timings. Thus speed enhancement can be achieved compared with a conventional detection system using a lock-in amplifier.

<<Processing in Computer PC>>

Figure 3:
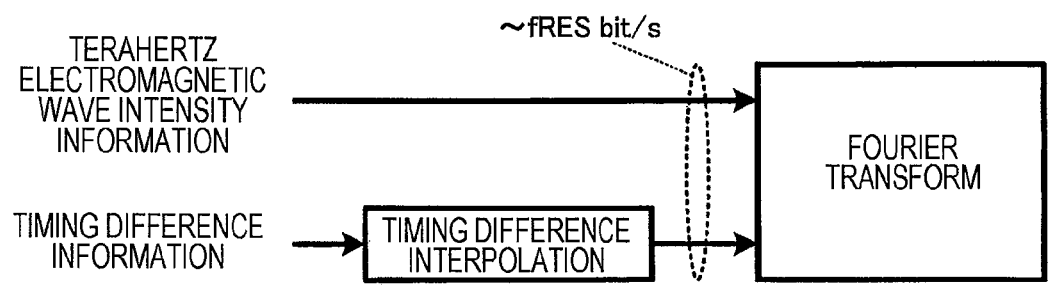
FIG. 3 is an explanatory diagram of a data processing method performed in a computer in the time-domain spectroscopy in FIG. 1.

FIG. 3 is a schematic diagram of processing executed in the computer PC 10. The computer PC 10 is fed information on the intensity of a pulsed terahertz wave outputted from the detector output processing unit, and information on the timing difference between pump light and probe light outputted from the mechanism for extracting timing difference information. The data rate of the intensity information is a rate up to a repetition frequency $f_{RES}$ of light pulses. The timing difference information has a data rate up to about three times $f_{CON}$, depending on the cutoff frequency of the LPF 3. The timing difference information is interpolated to the data rate of the intensity information to be in a one-to-one correspondence with the intensity information. A Fourier transform is implemented using both pieces of information to extract frequency and phase information, which is displayed on the display. The computer PC 10 is installed with software for executing the above-described processing. This can enhance the speed of analysis by the time-domain spectroscopy.

<<Effects of Example 1>>

Figure 4:
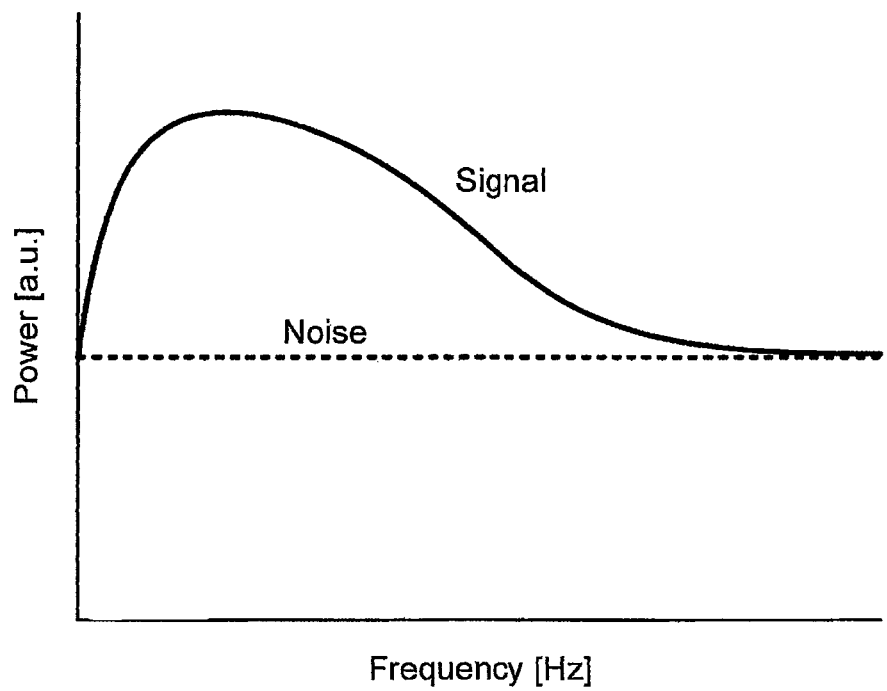
FIG. 4 is an explanatory diagram illustrating a frequency spectrum and noise after a Fourier transform obtained by a single delay time sweep when a conventional time-domain spectroscopy is used.
Figure 5:
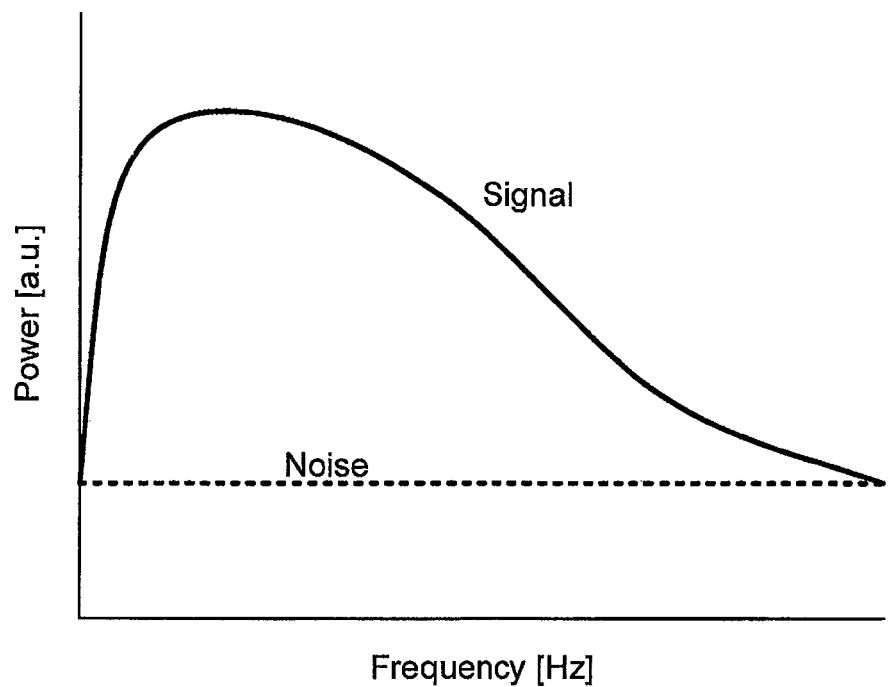
FIG. 5 is an explanatory diagram illustrating a frequency spectrum and noise after a Fourier transform obtained by a single delay time sweep when a time-domain spectroscopy in the present invention is used.

FIG. 4 is an example of a frequency spectrum of a pulsed terahertz wave analyzed without addition and averaging, using a time-domain spectroscopy before the present invention is applied thereto. A solid line indicates a signal, and a dotted line indicates noise. FIG. 5 is an example of a spectrum of a pulsed terahertz wave analyzed without addition and averaging, using the present invention. Compared with FIG. 4, noise can be reduced, a required SN ratio can be achieved even with a smaller number of times of addition, and analysis can be enhanced in speed.

Embodiment 2

Figure 6:
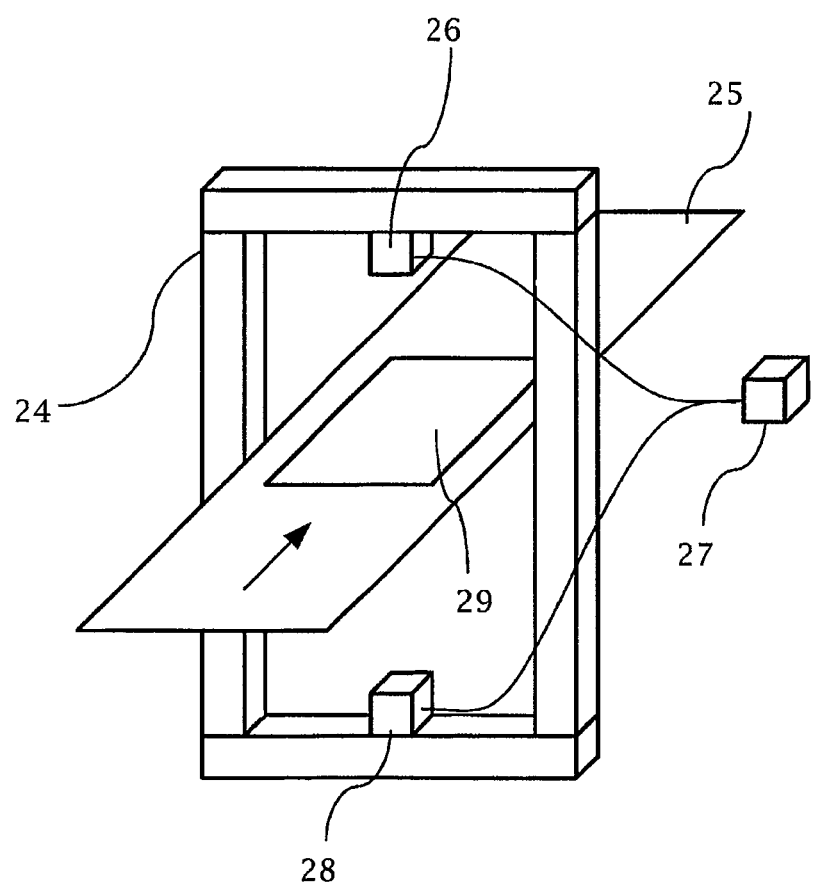
FIG. 6 is a diagram illustrating an example of a schematic configuration of a time-domain spectroscopic analysis system according to Embodiment 2 of the present invention.
Figure 7:
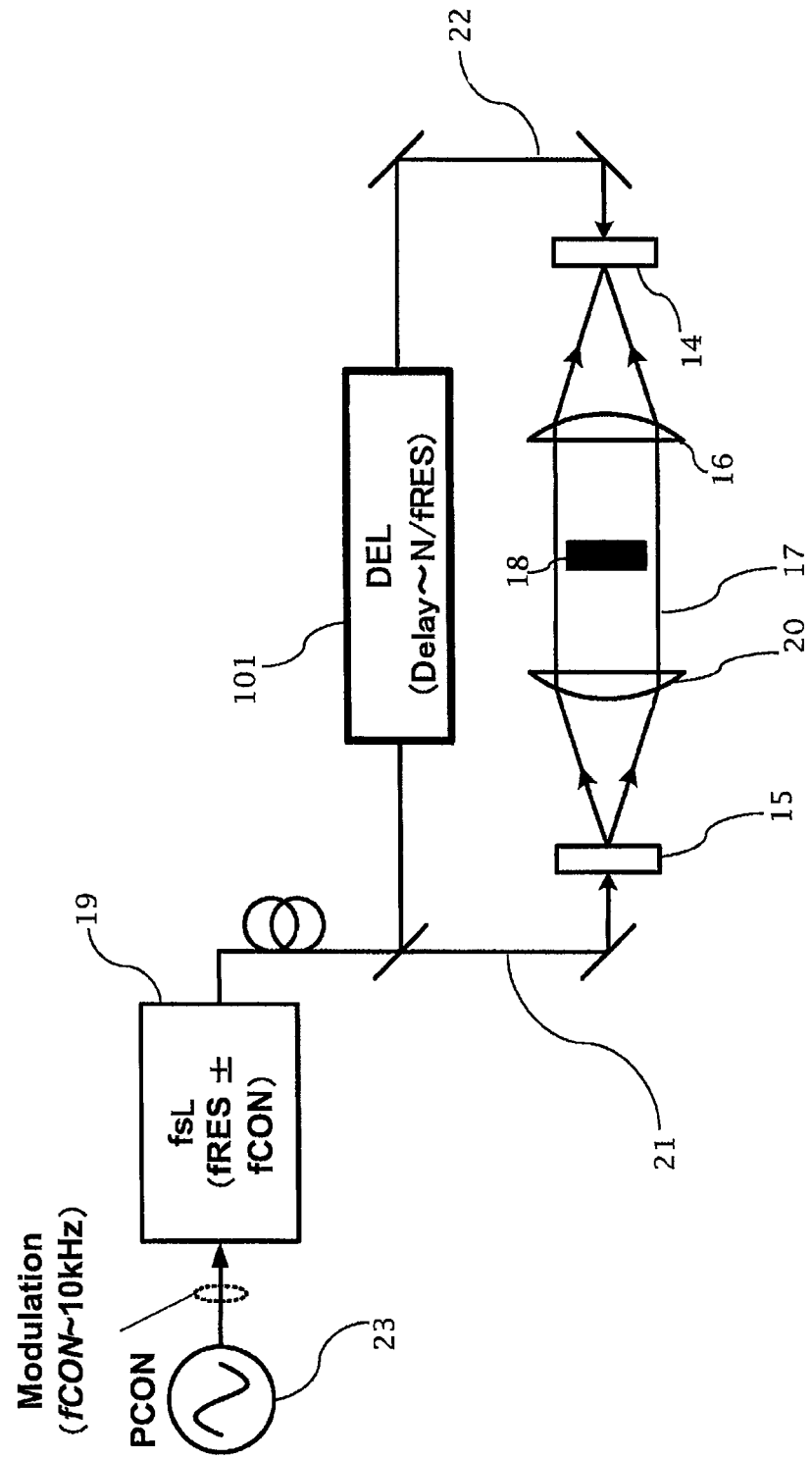
FIG. 7 is a block diagram illustrating an example of a schematic configuration of a time-domain spectroscopy considered as a premise of the present invention.
Figure 8:
FIG. 8 is an explanatory diagram illustrating pulse waveforms of pump light and probe light of the time-domain spectroscopy in FIG. 7.
Figure 9:
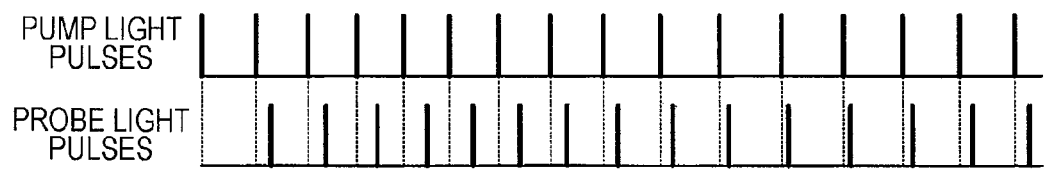
FIG. 9 is an explanatory diagram illustrating pulse waveforms of pump light and probe light when the time-domain spectroscopy in FIG. 7 is not in normal operation.
Figure 10:
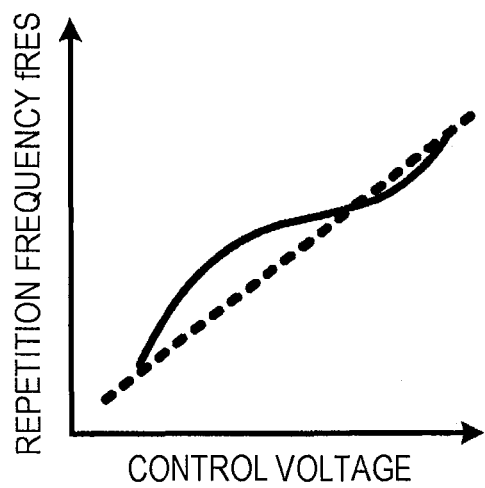
FIG. 10 is an explanatory diagram illustrating an example of the pulse repetition frequency control characteristics of a femtosecond pulse laser.
Figure 11:
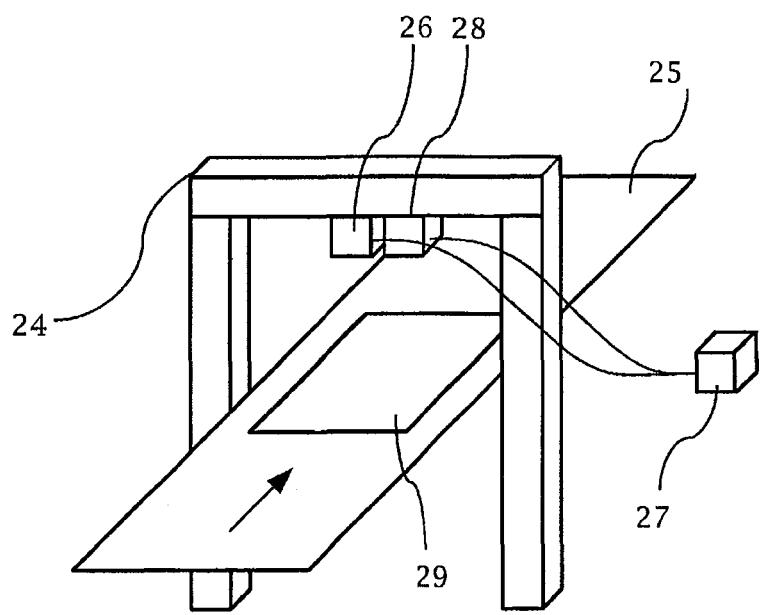
FIG. 11 is a diagram illustrating an example of a schematic configuration of a time-domain spectroscopic analysis system according to a modification of Embodiment 2 of the present invention.

FIG. 6 is a time-domain spectroscopic analysis system to which the time-domain spectroscopy in Example 1 is applied. The time-domain spectroscopy, a movable sample stage (MST) 25, and a terahertz electromagnetic wave sweep mechanism (terahertz-wave sweeper: TWS) 24 are included. On the MST 25, a measurement object 29 to be analyzed is placed. A terahertz electromagnetic wave generator 26 provided at the TWS 24 emits an electromagnetic wave pulse to the measurement object 29. The electromagnetic wave pulse having passed through the measurement object 29 enters a terahertz electromagnetic wave detector 28. At that time, when it is desired to detect a reflected wave or a scattered wave other than an electromagnetic wave having passed, the terahertz electromagnetic wave detector 28 may be provided on the terahertz electromagnetic wave generator 26 side of the measurement object 29 as in a modification (FIG. 11).

The terahertz electromagnetic wave generator 26 houses at least the GEN 15 and the PDET 12 used in Example 1, and the terahertz electromagnetic wave detector 28 houses at least the DET 14 and the PDET 13 used in Example 1. A processing unit 27 houses the laser 19, the computer 10, and others used in the time-domain spectroscopy in Example 1, which are optically or electrically connected to the terahertz electromagnetic wave generator 26 and the terahertz electromagnetic wave detector 28 to exchange signals.

The TWS 24 is a mechanism for sweeping a terahertz wave to the measurement object 29 in a direction perpendicular to a traveling direction.

To summarize the above, a time-domain spectroscopic analysis system in this example includes a time-domain spectroscopy including a splitter for splitting pulsed light entered, a variable delayer for delaying timing of a first part of the pulsed light split by the splitter, an electromagnetic wave generator for converting a second part of the pulsed light split by the splitter into an electromagnetic wave, a detector for detecting measurement data from a pulse having passed through a measurement object subjected to the electromagnetic wave emitted from the electromagnetic wave generator or a pulse reflected off the measurement object, and the pulse outputted from the variable delayer, and a comparator for detecting a phase difference between the pulsed light before being entered into the electromagnetic wave generator and the pulsed light outputted from the variable delayer, wherein a result obtained by the comparator is fed back to the variable delayer, a movable sample stage on which the measurement object is placed, and an electromagnetic wave sweep mechanism.

By using this time-domain spectroscopic analysis system, two-dimensional information on the measurement object 29 can be obtained in addition to the effects in Example 1. Further, high-speed analysis becomes possible.

REFERENCE SIGNS LIST

1 variable delayer (VDEL)
2, 3 low-pass filter (LPF)
4, 5 analog-to-digital converter (ADC)
6 detector output processing unit (OPU)
7 sample-and-hold circuit (SHC)
8 current-to-voltage conversion amplifier (IV-AMP)
9 phase comparator (PFD)
10 computer (PC)
11 display (DIS)
12, 13 photodetector(PDET)
14 pulse detector (DET)
15 pulse generator (GEN)
16, 17 lens
18 measurement object
19 femtosecond pulse laser
20 terahertz electromagnetic wave
21 pump light
22 probe light
23 light pulse period controller (PCON)
24 terahertz electromagnetic wave sweep mechanism (TWS)
25 movable sample stage (MST)
26, 27 terahertz time-domain spectroscopy (TDS)
29 measurement object
101 delayer (DEL)

The invention claimed is:

1. A time-domain spectroscopy, comprising:
a splitter for splitting pulsed light entered;
a variable delayer for delaying timing of a first part of the pulsed light split by the splitter;
an electromagnetic wave generator for generating an electromagnetic wave corresponding to a second part of the pulsed light split by the splitter;
a detector for detecting measurement data from a pulse having passed through a measurement object subjected to the electromagnetic wave emitted from the electromagnetic wave generator, and the pulse outputted from the variable delayer; and
a comparator for detecting a phase difference between the pulsed light before being entered into the electromagnetic wave generator and the pulsed light outputted from the variable delayer,
wherein a result obtained by the comparator is fed back to the variable delayer.

2. The time-domain spectroscopy according to claim 1, wherein data obtained by the comparator and the measurement data are used to obtain a measurement result of the measurement object.

3. The time-domain spectroscopy according to claim 1, further comprising a frequency filter, the frequency filter feeding back a mean value of the phase difference obtained by the comparator to the variable delayer.

4. The time-domain spectroscopy according to claim 3, wherein the frequency of a signal passed by the frequency filter is lower than the frequency of the pulsed light.

5. The time-domain spectroscopy according to claim 4, further comprising a first photodetector and a second photodetector, the first photodetector converting the pulsed light before being entered into the electromagnetic wave generator into an electrical signal, the second photodetector converting the pulsed light outputted from the variable delayer into an electrical signal, the electrical signals being fed into the comparator.

6. The time-domain spectroscopy according to claim 5, further comprising:
a laser for emitting the pulsed light; and
a period controller for outputting a voltage signal to control a pulse period of the laser,
wherein an output signal waveform from the period controller is one of a sign wave, a triangular wave, and a sawtooth wave.

7. A time-domain spectroscopy, comprising:
a splitter for splitting pulsed light entered;
a variable delayer for delaying timing of a first part of the pulsed light split by the splitter;
an electromagnetic wave generator for converting a second part of the pulsed light split by the splitter into an electromagnetic wave;
a detector for detecting measurement data from a pulse having passed through a measurement object subjected to the electromagnetic wave emitted from the electromagnetic wave generator, and the pulse outputted from the variable delayer; and
a comparator for detecting a phase difference between the pulsed light before being entered into the electromagnetic wave generator and the pulsed light outputted from the variable delayer,
wherein data obtained by the comparator and the measurement data are used to obtain a measurement result of the measurement object.

8. The time-domain spectroscopy according to claim 7, further comprising a frequency filter and an information processing unit,
wherein data obtained by the comparator passes through the frequency filter, and is subjected to information processing together with the measurement data in the information processing unit.

9. The time-domain spectroscopy according to claim 8, wherein the frequency of a signal passed by the frequency filter is higher than the frequency of the pulsed light.

10. The time-domain spectroscopy according to claim 9, further comprising a first photodetector and a second photodetector, the first photodetector converting the pulsed light before being entered into the electromagnetic wave generator into an electrical signal, the second photodetector converting the pulsed light outputted from the variable delayer into an electrical signal, the electrical signals being fed into the comparator.

11. The time-domain spectroscopy according to claim 10, further comprising:
 a laser for emitting the pulsed light; and
 a period controller for feeding a voltage signal to control a pulse period of the pulsed light into the laser,
 wherein an output signal waveform from the period controller is one of a sign wave, a triangular wave, and a sawtooth wave.

12. A time-domain spectroscopic analysis system, comprising:
 a time-domain spectroscopy comprising:
  a splitter for splitting pulsed light entered;
  a variable delayer for delaying timing of a first part of the pulsed light split by the splitter;
  an electromagnetic wave generator for converting a second part of the pulsed light split by the splitter into an electromagnetic wave;
  a detector for detecting measurement data from a pulse having passed through a measurement object subjected to the electromagnetic wave emitted from the electromagnetic wave generator or a pulse reflected off the measurement object, and the pulse outputted from the variable delayer; and
  a comparator for detecting a phase difference between the pulsed light before being entered into the electromagnetic wave generator and the pulsed light outputted from the variable delayer,
  wherein a result obtained by the comparator is fed back to the variable delayer;
 a movable sample stage on which the measurement object is placed; and
 an electromagnetic wave sweep mechanism.

* * * * *